United States Patent
Morrow et al.

(10) Patent No.: US 11,348,681 B1
(45) Date of Patent: May 31, 2022

(54) COMPUTERIZED RULE BASED SYSTEMS AND METHODS FOR PROVIDING INTERACTIVE HANDOFF PROTOCOL USER INTERFACES

(71) Applicant: TeleTracking Technologies, Inc., Pittsburgh, PA (US)

(72) Inventors: Raghen Morrow, Pittsburgh, PA (US); Deepak Bhurani, Pittsburgh, PA (US); Jamie Slater, Pittsburgh, PA (US); Patrick Sharbaugh, Pittsburgh, PA (US); Vipul Sinha, Pittsburgh, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 375 days.

(21) Appl. No.: 16/601,997

(22) Filed: Oct. 15, 2019

Related U.S. Application Data

(60) Provisional application No. 62/745,749, filed on Oct. 15, 2018.

(51) Int. Cl.
| | |
|---|---|
| *G16H 40/20* | (2018.01) |
| *A61B 5/00* | (2006.01) |
| *G06K 7/14* | (2006.01) |
| *G16H 10/60* | (2018.01) |

(52) U.S. Cl.
CPC ........... *G16H 40/20* (2018.01); *A61B 5/0022* (2013.01); *G06K 7/1413* (2013.01); *G16H 10/60* (2018.01)

(58) Field of Classification Search
CPC ...... G16H 40/20; G16H 10/60; A61B 5/0022; G06K 7/1413
See application file for complete search history.

(56) References Cited

U.S. PATENT DOCUMENTS

| | | | |
|---|---|---|---|
| 2009/0019552 A1* | 1/2009 | McLaughlin | G16H 10/60 726/27 |
| 2016/0098930 A1* | 4/2016 | Dillingham | G08G 5/0021 715/772 |

FOREIGN PATENT DOCUMENTS

CN 106101119 A * 11/2016

OTHER PUBLICATIONS

Giang, Wayne Chi Wei. "Supporting Transfer Time Predictions in Medical Dispatch Using Visualizations of Historical Data." University of Toronto (Canada). ProQuest Dissertations Publishing, 2018. 10932263 (Year: 2018).*

* cited by examiner

Primary Examiner — Linh Giang Le
(74) Attorney, Agent, or Firm — Ference & Associates LLC

(57) ABSTRACT

Systems and methods are disclosed for providing interactive handoff protocol user interfaces. In one embodiment, a computerized system may comprise a memory storing instructions, and a processor of a first electronic device. The processor may be configured to receive a pick-up request from a second electronic device, receive an acceptance indication for the pick-up request via an input device, provide a GUI prompting a scan of an identification tag on an individual, the GUI including at least one button in a non-selectable state, capture an image of the identification tag using the first electronic device, determine an identity of the individual based on the captured identification tag image, compare the determined identity to an identity in the received pick-up request, and modify the at least one button to a selectable state, wherein selection of the at least one button advances a handoff protocol for the individual.

13 Claims, 11 Drawing Sheets

COMPUTERIZED RULE BASED SYSTEMS AND METHODS FOR PROVIDING INTERACTIVE HANDOFF PROTOCOL USER INTERFACES

TECHNICAL FIELD

The subject matter described herein generally relates to electronic data processing and communication systems that employ rule sets to generate and provide graphical user interfaces (GUIs) for implementing handoff protocols, using real time data collected from a plurality of networked sources. More particularly, disclosed embodiments are directed to centralized communication systems for generating automated electronic messages if particular events are detected. The data processing system may automate one or more processes in response to the detected events and automatically distribute electronic messages to a plurality of networked devices.

BACKGROUND

Patients are frequently moved to numerous different locations in a medical facility such as a hospital. A patient may rest/sleep in a first location, then be transported to a second location for testing, transported to a third location for procedures and surgery, transported to a fourth location for recovery, and so forth. Indeed, modern hospitals move hundreds of patients around the facility every day, requiring frequent transportation of patients, equipment, and other items between points in the hospital.

Every time a patient is transported, there is a "handoff" of the patient from the caregiver who requested the transport to the transporter tasked with transporting the patient. A second handoff occurs from the transporter to the receiving caregiver. Each handoff involves the transfer of information about the patient such as special conditions and care considerations. The handoff process can cause delays in transporter workflow, significantly impacts the hospital's performance. Inaccurate and inconsistent handoff information can also adversely affect the patient's health. Thus, handoff of the incorrect patient, or improper handoff of a patient whose status was not sufficiently verified, can negatively impact the health of patients.

Traditional handoff protocols are manual processes that depend on the diligence and accuracy of the requesting/receiving caregiver and the transporter. Some current systems utilize computers to print information and manual checklists for transport requests, but these techniques still rely almost entirely on manual completion of the checklist. Hospital units and departments therefore lack systems that sufficiently ensure safe, accurate, and efficient patient handoff.

Some traditional techniques involve manual telephone calls, or paper-based manual transport requests. For example, in traditional systems, a transporter may accept a request by physically arriving at the patient's location and filling out paper forms. Hospital staff often review these forms under intense time pressure or while distracted, and may fail to spot mistakes in the information about the patient or even the identity of the patient. Current systems rely on human supervision to notice an error in part of the pick-up process, which requires additional review time by hospital staff. Moreover, even with human supervision, mistakes still occur, which result in delayed or improper care, which places strain on the system and can threaten the health of patients.

In view of the technical deficiencies of current systems discussed above, there is a need for improved computerized handoff techniques.

SUMMARY

Disclosed embodiments relate to systems and methods for uniform, centralized, and rule-based handoff protocol implementation, using interactive graphical user interfaces generated based on real-time data. Generated graphical user interfaces, coupled with real-time data collection and processing facilitates the implementation of handoff protocols that may be used when transferring a patient between a hospital caregiver and transporter. Disclosed embodiments may provide for enhanced accuracy and efficiency in the handoff protocol by dynamically varying the items that are displayed and selectable on electronic devices associated with the caregiver and transporter, to ensure consistency in the data received by a facility processor, and the accuracy of input data collected from multiple devices and sensors. The disclosed embodiments may automate the generation and transmission of some notifications for advancing through the handoff protocol.

Consistent with the present embodiments, a computerized system is disclosed. The computerized system may comprise a memory storing instructions, and a processor of a first electronic device in communication with a network. The processor may be configured to execute the stored instructions to receive, from a second electronic device via the network, a pick-up request, receive, via an input device in communication with the processor, an acceptance indication for the pick-up request, and provide a graphical user interface prompting a user to scan an identification tag on an individual, where the graphical user interface includes at least one button that is in a non-selectable state. The processor may capture, using the first electronic device, an image of the identification tag, determine, based on the captured identification tag image, an identity of the individual, verify the identity of the individual by comparing the determined identity to an identity in the received pick-up request, and modify the graphical user interface to change the at least one button to a selectable state, wherein selection of the at least one button advances the first electronic device to a first next step in a handoff protocol for the individual.

Consistent with the present embodiments, one or more computerized methods are disclosed, corresponding to the exemplary system disclosed above.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION OF EXEMPLARY EMBODIMENTS

Reference will now be made in detail to exemplary embodiments, examples of which are illustrated in the accompanying drawings and disclosed herein. Wherever convenient, the same reference numbers will be used throughout the drawings to refer to the same or like parts.

Figure 1:
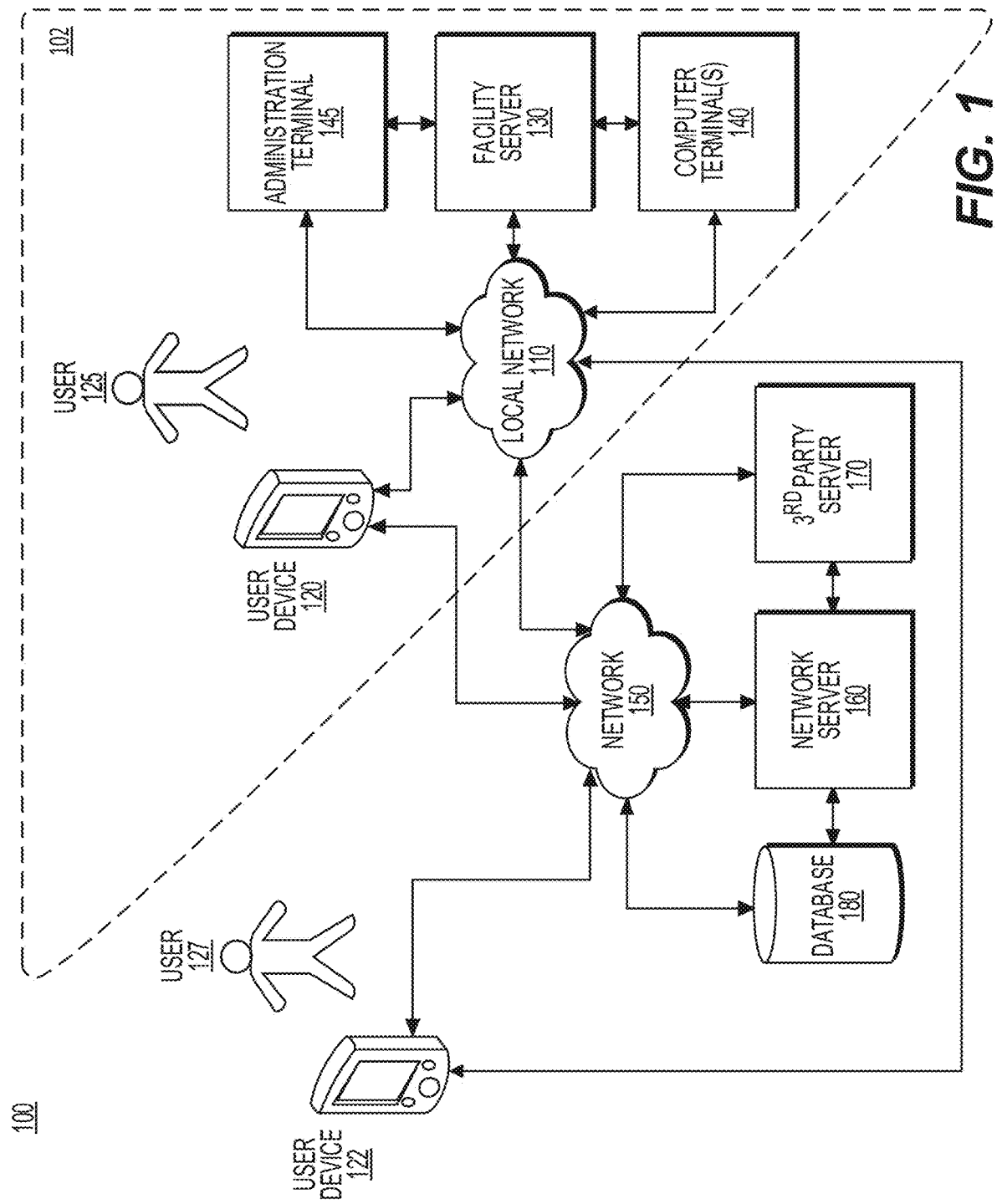
FIG. 1 depicts an example of a system environment for managing transport within a hospital, consistent with embodiments of the present disclosure.

FIG. 1 shows a diagram of a system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include a facility server 130, a computer terminal 140, an administration terminal 145, a first user device 120, a user second device 122, a network server 160, a third-party server 170, and a database 180. The components of system 100 may communicate directly, through a network 150, through a local network 110, or through a combination of communications methods. In some embodiments, local network 110, facility server 130, computer terminal 140, administration terminal 145, first user device 120, and second user device 122 may be physically disposed within a facility such as a hospital or office building (e.g. a facility system 102) while network 150, network server 160, third party server 170, and database 180 may be external to the facility. Other components known to one of ordinary skill in the art may be included in system 100 to perform tasks consistent with the disclosed embodiments. For example, in some embodiments, facility system 102 may include one or more sensor devices located throughout the facility to monitor one or more real-time or near real-time conditions such as occupancy, temperature, humidity, proximity, and other parameters indicative of a status or condition of a bed, room, area, equipment, or supplies. In some embodiments, sensors may also indicate the connection status of one or more devices, such as the connection of a blood pressure monitor cable to the monitor device. Moreover, sensor devices may monitor patient conditions such as heartbeat and blood oxygen saturation level. Additionally, in some embodiments facility system 102 may include one or more wireless receivers (not shown) configured to detect one or more wireless sensor or locating tags, to track a location of a tagged item and/or person, or a condition about the tagged item and/or person. The wireless receivers may be configured to detect objects and receive information through radiofrequency, infrared, radiofrequency-infrared hybrid, optical, ultrasound, Bluetooth™, and/or barcode.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message received from a computer terminal 140 may automatically associate the message with the room in which computer terminal 140 is installed.

Administrator terminal 145 may include a computer system or a device associated with a user 125 or 127 that manages or oversees a portion of facility system 102. For example, administrator terminal 145 may comprise a computer system located at a head nurse station, a transporter dispatch station, receiving department, or any other department manager's office or station.

User 125 or 127 may be one or more individuals associated with a patient to be transported. Users 125 and 127 may operate computer terminal 140, first user device 120, second user device 122, and/or another computer (not shown) to interact with system 100. Users 125 and 127 may be individuals located within and/or outside of the facility system 102, for example, transporters responsible for transporting patients and/or items. For example, users 125 and 127 may include physicians and nurses within the facility responsible for transporting the patients to different units. Users 125 and 127 may also include one or more individuals who may be responsible for assignments, such as transporting patients and/or items throughout a hospital (e.g., facility 102), or individuals who monitor the transportation of patients within the hospital. For example, users 125 and 127 may include doctors, nurses, porters, escorts, administrators, and/or volunteers. In some embodiments, one or more additional users may interact with one or more devices of system 102, such as individuals having personal relationships with the patients (e.g. family members) and referring individuals (e.g. outside physicians and medics).

System 100 may be customizable and provide individualized access for each user 125 and user 127. For example, in some embodiments, only certain users 125 and 127, such as physicians and nurses, may be allowed to generate transport requests. In some embodiments, user 125 or 127, such as the patient's primary physician, may be required to authorize all requests. User 125 or 127 may be solely responsible for specific tasks, such as a transport assignment, may have access limited to perform their responsibilities. Users 125 or 127 may have certain access permissions and abilities within system 100 restricted depending on their role identified in one or more databases, associated with a role in the handoff process. For example, in some embodiments, transporter users may be provided with selectable options and fields for confirming that a patient's lines, tubes, and other connections are secure prior to transport, whereas a caregiver user may be provided with a different set of selectable options and capabilities in the displayed graphical user interfaces. Thus, the system may dynamically configure the options available to a certain user in the handoff process based on their role identified by the system 100.

First user device 120 and second user device 122 may be personal computing devices such as, for example, a general purpose or notebook computer, a mobile device with computing ability, a tablet, a smartphone, wearable device such as a head-mounted smart display device a smart watch, or any combination of these computers and/or affiliated components. In some embodiments, first user device 120 or second user device 122 may be a computer system or mobile computer device that is operated by user 125 or 127. In some embodiments, first user device 120 or second user device 122 may be associated with a particular individual such as user 125 or 127, such that messages and/or task assignments directed toward user 125 or 127 are sent to first user device 120 or second user device 122. In some embodiments, first user device 120 or second user device 122 may communicate with facility server 130 and/or network server 160 via direct wireless communication links (not shown), or via a combination of one or more of local network 110 and/or network 150.

Facility server 130 may be operated by a facility such as a hospital. Facility server 130 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth™' Ethernet, and other suitable short-range connections that enable computer terminal 140 and first user device 120 to send and receive information between the components of system 100. In some embodiments, local network 110 may be excluded, and computer terminal 140 and first user device 120 may communicate with system 100 components via network 150. In some embodiments, computer terminal 140 and/or first user device 120 may communicate with one or more system 100 components via a direct wired or wireless connection. In some embodiments, such arrangements may also apply to second user device 122.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service™, Azure Mobile Services™, or Google Cloud Messaging™. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
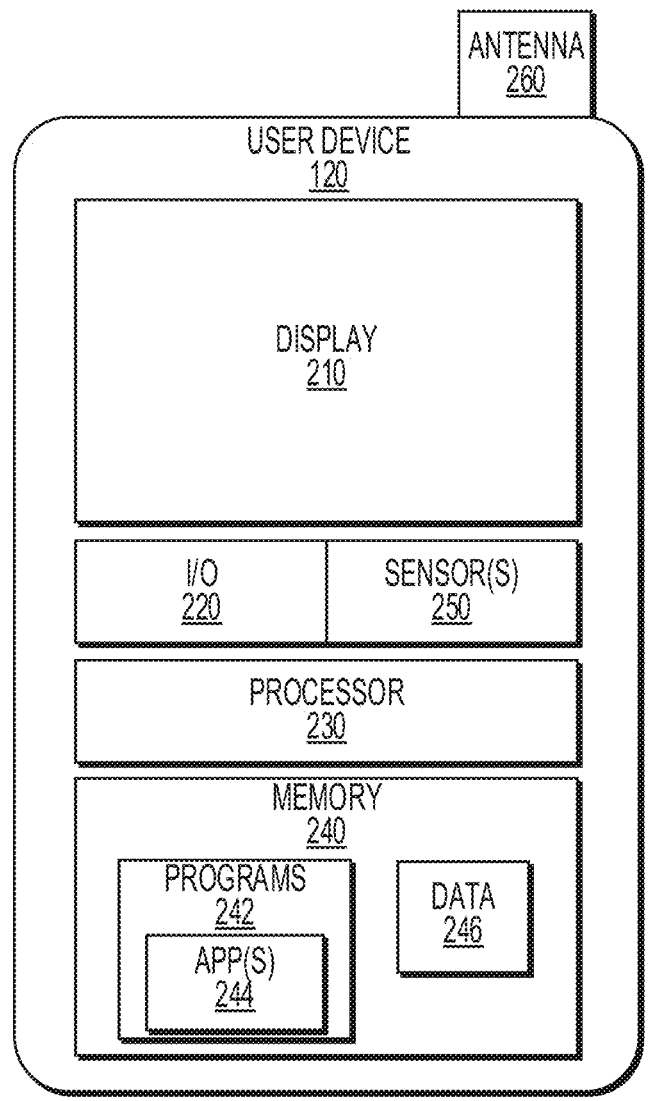
FIG. 2 depicts an example of a user device, consistent with embodiments of the present disclosure.

FIG. 2 shows a diagram of an exemplary first user device 120, consistent with disclosed embodiments. Second user device 122 may have similar components and configurations. As shown, first user device 120 may include display 210, I/O device(s) 220, processor 230, memory 240 having stored thereon data 246 and one or more programs 242, such as app(s) 244, sensor(s) 250, and antenna 260.

Display 210 may include one or more devices for displaying information, including but not limited to, liquid crystal displays (LCD), light emitting diode (LED) screens, organic light emitting diode (OLED) screens, and other known display devices.

I/O devices 220 may include one or more devices that allow mobile device 120 to send and receive information. I/O devices 220 may include, for example, a pointing device, keyboard, buttons, switches, and/or a touchscreen panel. I/O devices 220 may also include one or more communication modules (not shown) for sending and receiving information via antenna 260 from other components in system 100 by, for example, establishing wired or wireless connectivity between first user device 120 to local network 110, network 150, or by establishing direct wired or wireless connections between first user device 120 and other components of system 100. Direct connections may include, for example, Bluetooth™, Bluetooth LE™, WiFi, near field communications (NFC), or other known communication methods which provide a medium for transmitting data between separate devices.

Processor 230 may be one or more known processing devices, such as microprocessors manufactured by Intel™ or AMD™ or licensed by ARM. Processor 230 may constitute a single core or multiple core processors that executes parallel processes simultaneously. For example, processor 230 may be a single core processor configured with virtual processing technologies. In certain embodiments, processor 230 may use logical processors to simultaneously execute and control multiple processes. Processor 230 may implement virtual machine technologies, or other known technologies to provide the ability to execute, control, run, manipulate, store, etc. multiple software processes, applications, programs, etc. In another embodiment, processor 230 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein. Memory 240 may include a volatile or non-volatile, magnetic, semiconductor, tape, optical, removable, non-removable, or other type of storage device or tangible (i.e., non-transitory) computer-readable medium that stores one or more program(s) 242, such as app(s) 244, and data 246. Data 246 may include, for example, hospital information, patient information, user information, task information, and display settings and preferences. For example, data 246 may include information related to patients and items to be transported, data 246 may also include information related to staff scheduling. In some embodiments, data 246 may further include one or more rules for analyzing and generating a task, such as a transportation assignment.

In some embodiments, first user device 120 may contain one or more sensors 250 for collecting environmental, movement, and/or security data. Sensors 250 may include: one or more environmental sensors such as, for example, heartbeat sensors, oxygen sensors, ambient light sensors, camera, optical detector, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 230 may use data collected by sensors 250 to control or modify functions of program(s) 242.

As discussed below, one or more graphical user interfaces may be generated and displayed on first user device 120 and/or second user device 122. For example, if first user device 120 is associated with a user who is a transporter for hospital patients and equipment, an application running on first user device 120 may generate and provide one or more interactive graphical user interfaces for providing instructions and indications to the transporter, and for collecting and receiving data associated with the handoff protocol for the patient. In some embodiments, a handoff protocol may be predetermined and stored in system 100, based on the needs and configuration of the particular facility. In some embodiments, the handoff protocol may be generated automatically based on the patient condition and status. For example, a patient diagnosed with a certain condition may require special procedures and/or equipment. Facility system 102 may query one or more lookup tables or stored rule sets to identify a predetermined handoff protocol or predetermined handoff protocol steps associated with the patient condition. In some embodiments, facility system 102 may also select a handoff protocol or handoff protocol steps based on the originating and destination locations for the patient. For example, if facility system 102 receives a transport request for a patient from their room to a lab that is not equipped with oxygen tanks, then facility system 102 may utilize one or more rule sets or lookup tables to determine that the patient must be transported with a larger/fuller oxygen tank. Facility system 102 may then add a handoff protocol step that ensures the sufficient level of oxygen is transported with the patient.

Figure 3:
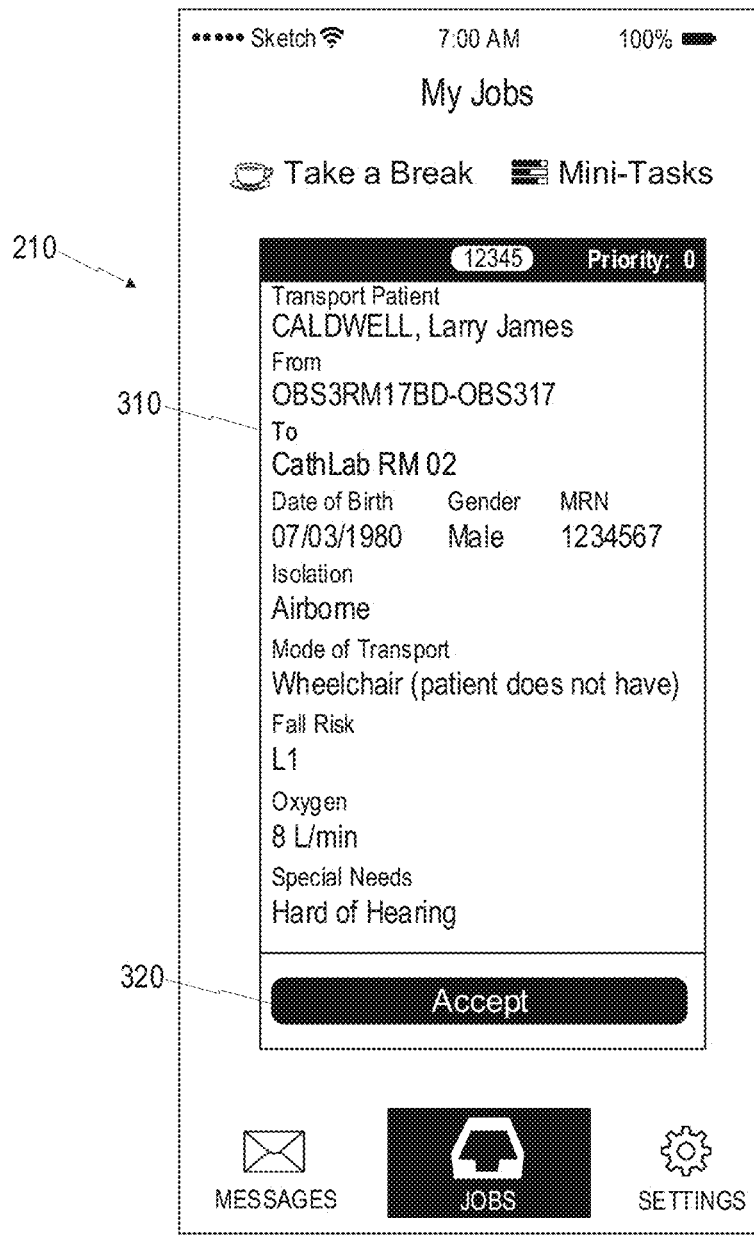
FIG. 3 is an illustration of an example of an accept job mobile device user interface, consistent with embodiments of the present disclosure.

FIG. 3 shows an illustration of an example of an "accept job" user interface, consistent with embodiments of the present disclosure. In some embodiments, a user device such as first user device 120 or second user device 122 may cause display 210 to display particular GUIs, such as the one shown in FIG. 3. As shown in FIG. 3, one such GUI may include a transport request info panel 310 and an accept button 320. In the example shown in FIG. 3, the "accept job" graphical user interface (GUI) may be displayed on the user device associated with a transporter. Upon receiving an indication from the transporter that the job is accepted (by activation of accept button 320, one or more applications running on the transporter's user device may prevent the display or possible acceptance of additional transport tasks, until the presently accepted task is complete or otherwise cancelled.

In some embodiments, display 210 may display the "accept job" GUI following a pickup request made by user 127, who may be a caregiver, such as a nurse. Information displayed transport request info panel 310 as part of the accept job mobile device interface may include information relating to a patient's transport, such as the time of an appointment at a receiving unit. In some embodiments, user 125, who may be a transporter accepting a transport job in a hospital, may accept a transport request from a user 127, who may be a caregiver, by selecting accept button 320. A user 125 may select the accept button 320 using a touchscreen, mouse, keyboard, or other device capable of input to first user device 120. Thereafter, first user device 120 may generate and transmit a notification to facility server 130 and/or a second user device associated with the requesting caregiver, to indicate that the transport request has been accepted and initiated.

In some embodiments, upon detecting selection of the accept button 320, first user device 120 may generate and display one or more GUIs providing the steps of the handoff protocol selected by facility server 130, changing the content displayed on display 210. In some embodiments, first user device 120 may iteratively display different GUIs corresponding to each step and inquiry in the selected handoff protocol. Each GUI may include a selectable button for advancing to the next step in the protocol, such as a "Complete" button, a "Go-in-progress" button, or another button representing the completing of a particular step in the protocol, hereinafter referred to as "advance" buttons. First user device 120 may prevent selection of an advance button on the GUI until first user device 120 and/or facility server 130 verifies that all required information has been entered and is accurate. Similarly, first user device 120 may prevent selection of accept button 320 if a device in system 100, such as another first user device 120 or second user device 122, has not received a complete entry of information, or has received a transport process cancellation, from a user 125 or 127. In such embodiments, first user device 120 and/or facility server 130 maintains a record related to a transport job, which contains a notation of the current state of a transport job. For example, the state of a transport job may be "Presented," "Accepted," Waiting on Caregiver Handoff, " In Progress," Waiting on Receiver Handoff," "Complete," or others. In some embodiments, first user device 120 and/or facility server 130 evaluates a record when determining whether to process a state transition. If first user device 120 and/or facility server 130 determines that the handoff procedures required for a state transition are met, it may modify the record and permit display 210 to provide a new GUI that reflects a new state reflecting advancement in the handoff protocol. If first user device 120 and/or facility server 130 determines that required handoff procedures have not been met, the record may not be changed, and display 120 may not change to a GUI reflecting a new state. Display 120 may also display a notification indicating that the record has not been changed, and/or that a state transition has not occurred. If a state transition is not processed, first user device 120 and/or facility server 130 may prevent display 210 from changing to a new GUI in the transport protocol process, may prevent recognition of an input selecting the accept button 320 or advance button, and may alter the display of the accept button 320 or advance button to indicate to a user that the button is not yet selectable. Disclosed embodiments may perform these sub-steps constantly, to ensure accuracy in the entered data and completion of data entry/verification before allowing the handoff protocol to advance.

In some embodiments, any number of sensors, such as those described with respect to facility system 102 in FIG. 1, may communicate with first user device 120 or facility server 130, to provide information about the patient. In some embodiments, first user device 120 and/or facility server 130 may alter the ability to receive an indication of selecting the accept button 320, if a sensor detects a significant deviation from "normal" in a patient condition, such as a patient's heartbeat being outside an acceptable range, or another alarm condition. Accordingly, the disclosed embodiments may prevent initiation of a handoff protocol when the patient is determined to be unsafe for moving. In some embodiments, an alarm condition detected from received sensor data may halt the handoff process at any step, and may cause the generation and display one or more GUIs associated with the detected alarm condition. In some embodiments, a first user device 120 may not allow the transporter (such as user 125) to advance to a subsequent step if the patient is not located within a particular area in a hospital, such as the patient's room. In such embodiments, first user device 120 (or facility server 130) may detect a location of the first user device 120 within the hospital using a GPS-enabled device, indicating that a patient's location is outside a particular area in the hospital, or a triangulation or proximity-based location system. If the first user device 120 (and presumably also the transporter user) are not located in the proper location for the next step in the handoff protocol, then first user device 120 may prevent selection of an advance button, or prevent entry of information, until first user device 120 is sufficiently proximate to the patient location. In response to this determination, a first user device 120 may place the halt command on a program 242. Accordingly, the disclosed embodiments may prevent improper advancement of the handoff protocol or entry of information until the system is certain that the first user device 120 is located in the proper location for completing the handoff steps (such as being with the patient to enter patient identification information).

In some embodiments, a notification may be sent to a first user device 120, or other device in system 100, such as a computer terminal 140 indicating a new transport request. The transport request may be generated automatically by facility server 130, or received from a second user device 122 associated with a user 127 such as a caregiver. In some embodiments, a notification may be sent to second user device 122, facility server 130, or other device in system 100 such as a computer terminal 140, indicating the acceptance of the transport request. This acceptance notification may be generated based on a detected selection of accept button 320. In some embodiments, a notification may include information relating to the transport job, such as estimated time of completion, a criticality status of the transportation job, or any delays or problems encountered.

Following the acceptance of the transport request, first user device 120 may generate and display a GUI (not shown) indicating the current location of the patient, and provide information about the transportation job. First user device 120 may receive an indication that the transporter carrying first user device 120 has reached the patient to be transported. The indication may be received based on a proximity between first user device 120 and one or more location sensors associated with the patient, or by a received input indicating that the transporter has arrived at the patient.

Figure 4:
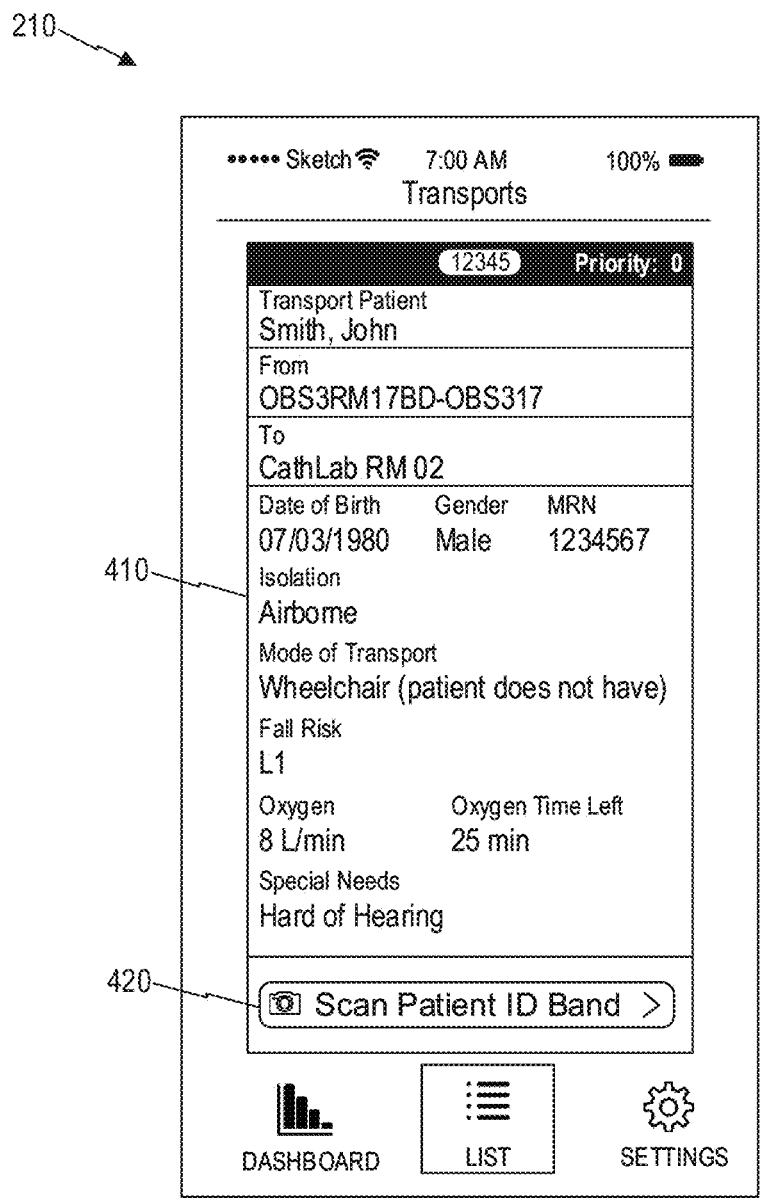
FIG. 4 is an illustration of an example of a scan patient ID band request mobile device user interface, consistent with embodiments of the present disclosure.

After determining that first user device 120 has arrived at the patient, first user device 120 may generate and provide a GUI requiring identification of the patient to be transported. FIG. 4 shows an illustration of an example of a scan patient ID GUI, to prompt the collection about identifying information for the patient. As shown in FIG. 4, one such GUI may include a patient info panel 410 and a scan patient ID band accept button 420. In some embodiments, second user device 122, such as a smartphone associated with the requesting caregiver or other caregiver handling the outbound transfer, may also generate and display a similar GUI prompting the caregiver to collect identifying information about the patient. Thus, the disclose system may prompt multiple users (including the transporter and the requesting caregiver) to obtain and enter identifying information for the patient, ensuring accuracy in the patient to be transported, and ensuring that the data is received from multiple individuals within a predetermined timeframe.

As discussed above, in some embodiments, the scan patient ID GUI may be displayed following an acceptance of a pickup request by a user 125, who may be a transporter in a hospital. In other embodiments, display 210 may display this GUI after a second user device 122 receives information from first user device 120. Information displayed on patient info panel 410 as part of the scan patient ID band request mobile device interface may include information entered by the requesting caregiver. In some embodiments, first user device 120 (or second user device 122) may activate a camera or other optical sensor embedded in the device, to capture an image of a patient ID. In some embodiments, a peripheral of computer terminal 140 may include a camera or optical sensor capable of scanning the patient ID. First user device 120 may detect selection of the accept button 420 using a touchscreen, mouse, keyboard, or other device capable of input to first user device 120. Responsive to the detected selection, first user device 120 may scan the patient ID, and first user device 120 or facility server 130 may determine the identity of the patient based on the scanned patient ID. In some embodiments, the scanned patient ID may be a barcode, Quick Response (QR) code, or other encrypted identification information, and first user device 120/facility server 130 may interpret the scanned code to determine the patient ID. In other embodiments, first user device 120 or facility server 130 may perform optical character recognition of text and numbers on a patient wristband or other tag, to determine the patient identity.

In some embodiments, a transporter (such as user 125) or requesting/sending caregiver (such as user 127) may attempt to select scan patient ID band accept button 420 to advance to a subsequent step in a patient transport process, which may change the content displayed on display 210 to show new information. In some embodiments, a first user device 120 or second user device 122 may not allow the user from selecting scan patient ID band accept button 420 and advancing the handoff protocol by placing a halt command on a program 242. Such a halt command may prevent display 210 from displaying a new GUI. In some embodiments, a first user device 120 or second user device 122 may place this command if a device in system 100, such as another first user device 120 or second user device 122, has not received a complete entry of information, or has received a transport process cancellation, from a user 125 or 127.

In some embodiments, any number of sensors, such as those described with respect to facility system 102 in FIG. 1, may provide data to first user device 120 and/or facility server 130 that may cause first user device 120 and/or facility server 130 to prevent selection of scan patient ID band accept button 420. For example, sensors may provide data indicating a significant deviation in a patient condition, such as a patient's heartbeat being outside an acceptable range.

In some embodiments, a notification may be sent from first user device 120 to facility server 130 and/or second user device 122 (such as a requesting/sending caregiver's device), indicating that first user device 120 has scanned, or is attempting to scan, a patient wristband ID. Similarly, the caregiver's device may send a similar notification to first user device 120 and/or facility server 130 indicating that the caregiver's user device has scanned the patient wristband ID. This notification may be triggered in response to selection of scan patient ID band accept button 420. In some embodiments, a notification may include the completion status of the patient ID scan, the determined patient identification resulting from an analysis of the scanned ID, or information about any delays or problems encountered by the system.

Figure 5:
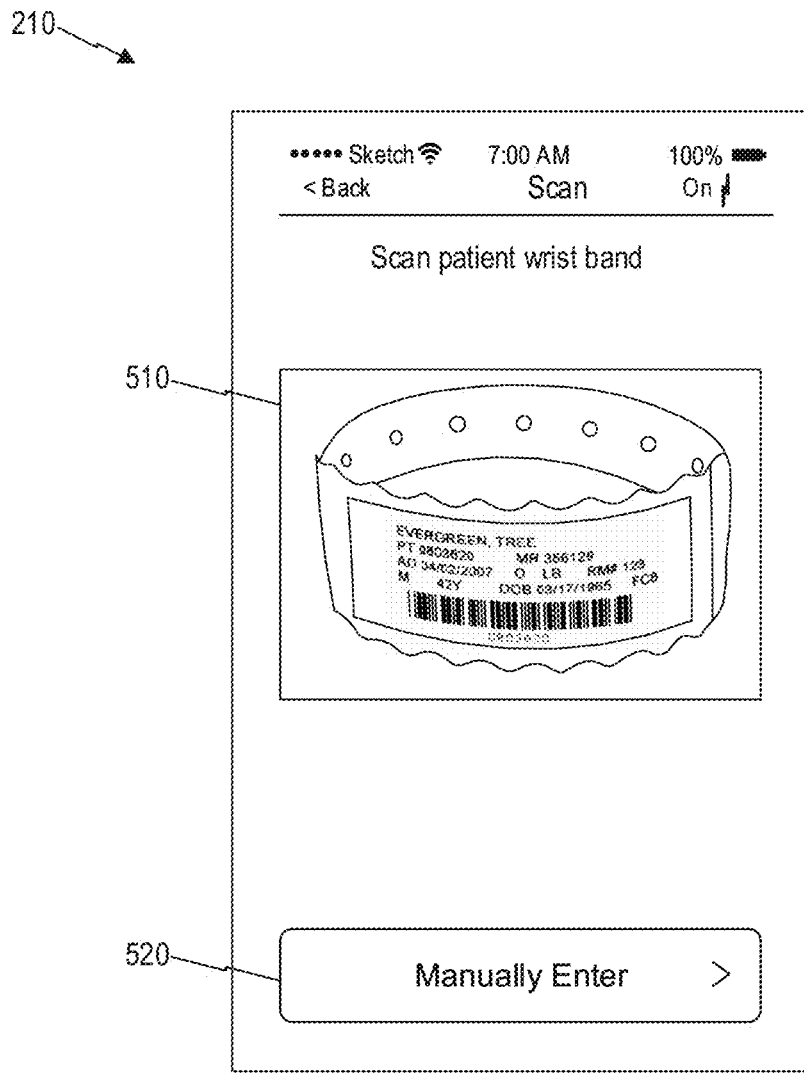
FIG. 5 is an illustration of an example of a scan patient ID band mobile device user interface, consistent with embodiments of the present disclosure.

FIG. 5. is an illustration of an example of a scan patient ID band mobile device user interface, consistent with embodiments of the present disclosure. First user device 120 or second user device 122 may display the scan patient ID GUI to allow a user to position the patient ID band within the view of a camera or other optical sensor in the respective device. As shown in FIG. 5, one such GUI may include a patient wristband scan panel 510 and a manual entry button 520.

In some embodiments, first user device 120 may provide the scan patient ID GUI on display 210 following the acceptance of a scan patient ID band request by the transporter user. First user device 120 (for the transporter) or second user device 122 (for the caregiver) may show information on display 210 in the patient wristband scan panel 510 that includes real-time image or video content captured by the first user device 120 camera, or other device capable of capturing such content. In some embodiments, this content may be captured from a camera, which may be a sensor 250, connected to a first user device 120 or second user device 122. In some embodiments, image or video content of a patient wristband is sent to processor 230, and a program 242 determines whether a patient identifier, such as a unique barcode, QR code, or other identifying textual information, is present in the image or video content. In other embodiments, this determination may be made by another processor on another device, such as facility server 130 or network server 160. In some embodiments, display 210 may provide additional information determined based on the captured image or video content received. For example, a green box or other indicator of a successful scan of a patient wristband may appear in patient wristband scan panel 510 to indicate the successful scan and analysis of the patient ID band. In some embodiments, first user device 120 may detect a selection of manual entry button 520, such as if the patient ID band cannot be scanned.

After detecting a selection of manual entry button 520, first user device 120 may provide an information entry interface, prompting the entry of identifying information associated with the patient to be transported.

In some embodiments, first user device 120 may dynamically alter the displayed GUI, such as by changing the appearance to prevent selection of manual entry button 520. In such embodiments, button 520 may be rendered unselectable if first user device 120 or facility server 130 determines that readable patient wristband information has already been captured and processed using the scan function.

In some embodiments, a notification may be sent to second user device 122, or other point in system 100, such as a computer terminal 140, indicating that a user 125 has attempted to scan a patient wristband, or has successfully scanned a patient wristband. This notification may be triggered after a first user device 120 or second user device 122 has received image or video data captured from a camera or other sensor 250, or from a manual entry initiated by the detected selection of manual entry button 520. In some embodiments, a notification may also include information relating to the transport job, such as estimated time of completion, a critical status of the transportation job, or any delays or problems encountered.

Figure 6:
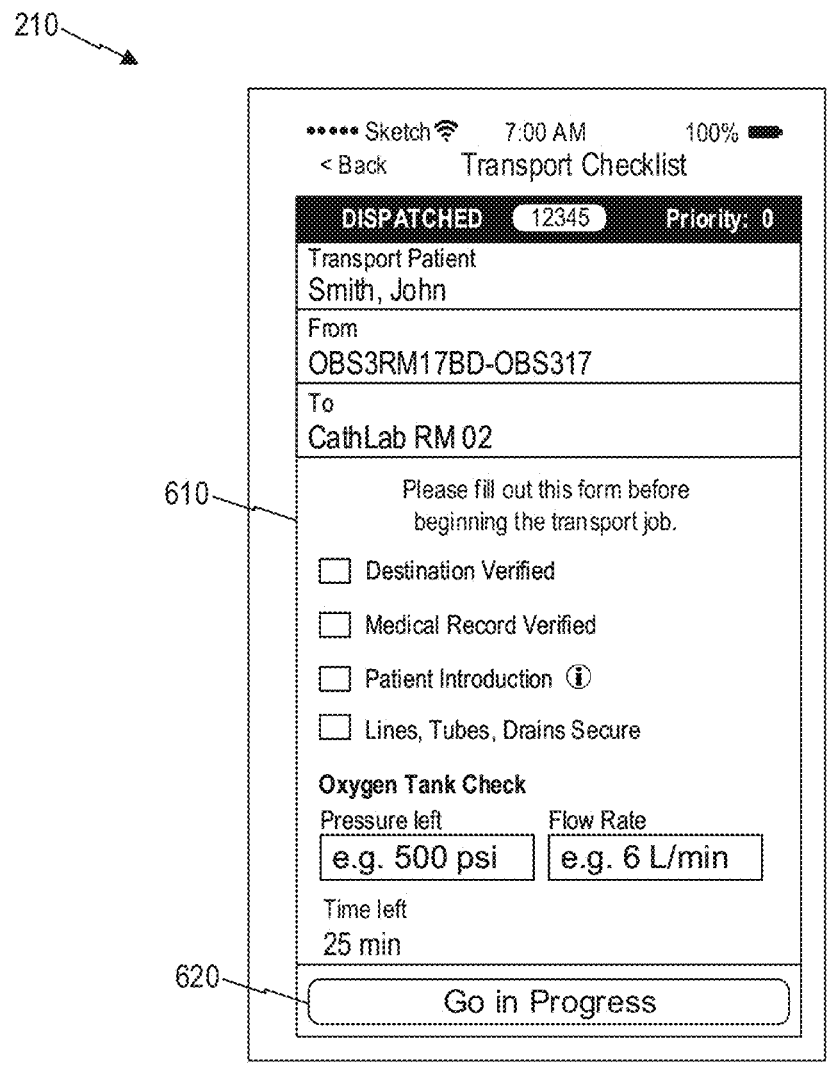
FIG. 6 is an illustration of an example of a go in progress mobile device user interface, consistent with embodiments of the present disclosure.

FIG. 6 shows an illustration of an example of a transport checklist GUI, consistent with embodiments of the present disclosure. In some embodiments, first user device 120 associated with a transporter, may display the transport checklist GUI. As shown in FIG. 6, one such GUI may include a patient data entry and info panel 610 and an advance button such as go-in-progress button 620.

In some embodiments, first user device 120 or second user device 122 may produce the GUI shown in FIG. 6 on display 210 after receiving image data relating to a patient wristband ID, described with respect to FIG. 5. In some embodiments, first user device 120 or second user device 122 may receive data related to a patient, such as an oxygen tank pressure level and oxygen flow rate associated with a patient, based on received input into info panel 610 by the transporter or caregiver. In some embodiments, first user device 120 may receive an indication to advance the handoff protocol based on a selection of go-in-progress button 620, which may be made by the transporter or caregiver associated with the patient, using a touchscreen, mouse, keyboard, or other device capable of input to first user device 120.

In some embodiments, first user device 120 may progress to a new part of the transport process and change content shown on display 210 when it receives an input from go-in-progress button 620 after interaction by a user 125 or 127. In some embodiments, a first user device 120 may not allow a user 125 or a user 127 to select go-in-progress button 620 and advance to a subsequent step in the patient handoff protocol by placing a halt command on a program 242, preventing display 210 from displaying a new GUI. In some embodiments, a first user device 120 or second user device 122 may place such a command if a device in system 100, such as another one of first user device 120 or second user device 122, has not received a complete entry of information on the GUI, has received a transport process cancellation request, or an indication of an alarm condition.

In some embodiments, a notification may be sent to first user device 120 or second user device 122, or other point in system 100, such as a computer terminal 140, indicating that a first user device 120 or second user device 122 has received patient information. This notification may be triggered after a user 125 or 127 selects go-in-progress button 620. In some embodiments, a notification may include patient information, as well as information relating to the transport job, such as estimated time of completion, a critical status of the transportation job, or any delays or problems encountered.

Figure 7:
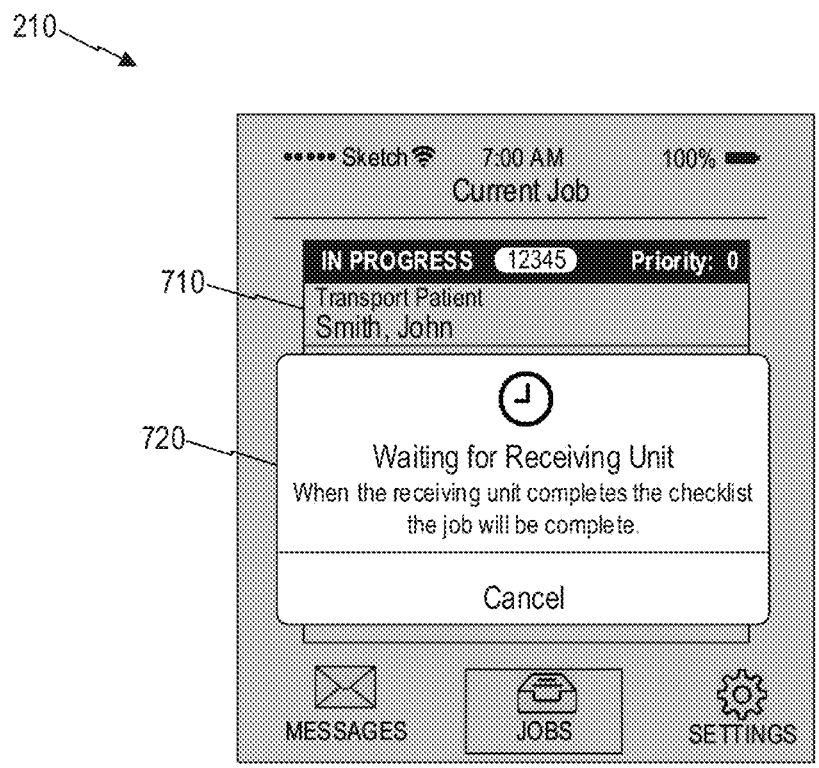
FIG. 7 is an illustration of an example of a waiting on other user mobile device user interface, consistent with embodiments of the present disclosure.

FIG. 7 shows an illustration of an example of a waiting status GUI. The waiting status GUI may be displayed on first user device 120 or second user device 122 to inform the associated user that one or more actions are required by another user before the handoff protocol may proceed. For example, second user device 122 may require additional information about the patient to be transported, and first user device 120 may display the waiting status GUI until facility server (or another connected processor) determines that second user device 122 has received all required data and indications. As shown in FIG. 7, one such GUI may include a background info panel 710 and a waiting notification 720.

In some embodiments, first user device 120 may produce the waiting status GUI on display 210 while another device (such as second user device 122) is awaiting input from another user or sensor device. In some embodiments, a first user device 120 may display background info panel 710 and waiting notification 720, to prevent display 210 from displaying a new GUI or allowing selection of content on the current GUI. In such embodiments, first user device 120 may not display a different GUI until a device in the system, such as first user device 120 or computer terminal 140 has received information from a second user device 122, such as an indication that a patient's medical record is verified. Second user device 122 may receive this information as described regarding FIG. 6.

In some embodiments, a user such as the transporter may not be able to input new information while waiting notification 720 is displayed. In other embodiments, the user may be able to select an option, such as a cancel option, prompting first user device 120 to revert to a previous GUI, before until the pending tasks on second user device 122 are verified as completed.

When waiting notification 720 is displayed, a notification may be sent to other devices in system 100, such as second user device 122 or computer terminal 140. In some embodiments, a notification may include a transport job status, estimated time of completion, a critical status of the transportation job, any delays or problems encountered, or patient information.

Figure 8:
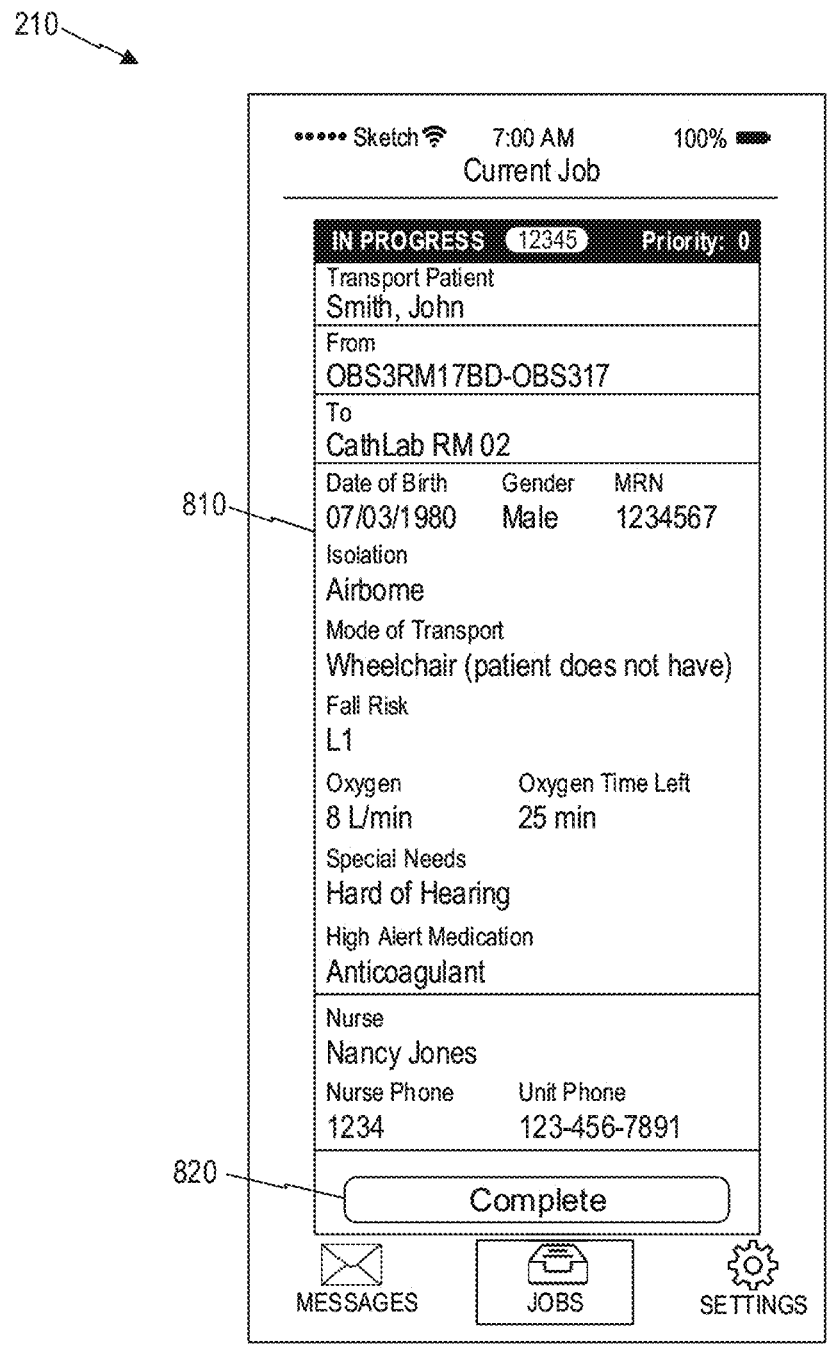
FIG. 8 is an illustration of an example of a complete job mobile device user interface, consistent with embodiments of the present disclosure.

FIG. 8 shows an illustration of an example of a completion GUI, consistent with embodiments of the present disclosure. In some embodiments, first user device 120 may display the completion GUI. As shown in FIG. 8, one such GUI may include a transport job info panel 810 and a completion button 820.

In some embodiments, first user device 120 may provide the completion GUI on display 210 including information entered by user such as the transporter or a receiving caregiver. In contrast to the requesting/sending caregiver, the receiving caregiver may be a nurse or other hospital employee located at the destination location for the patient transport, who accepts the transported patient into their custody. Information displayed on transport job info panel 810 as part of the completion confirmation mobile device user interface may include information entered by a user 125, such as a transporter, or a user 127, such as a caregiver or receiver. In some embodiments, first user device 120 detect selection of completion button 820 by the transporter indicating completion of the transport job in a hospital.

In some embodiments, first user device 120 may indicate to facility server 130 that the transport protocol is complete, and change content shown on display 210 responsive to selection of completion button 820, such as by causing display 210 to display an image indicating that the job is complete. In some embodiments, after first user device 120 has received selection of completion button 820, a notification may be sent to second user device 122, or other point in system 100, such as a computer terminal 140, indicating that the transport job has been completed by the transporter.

Figure 9:
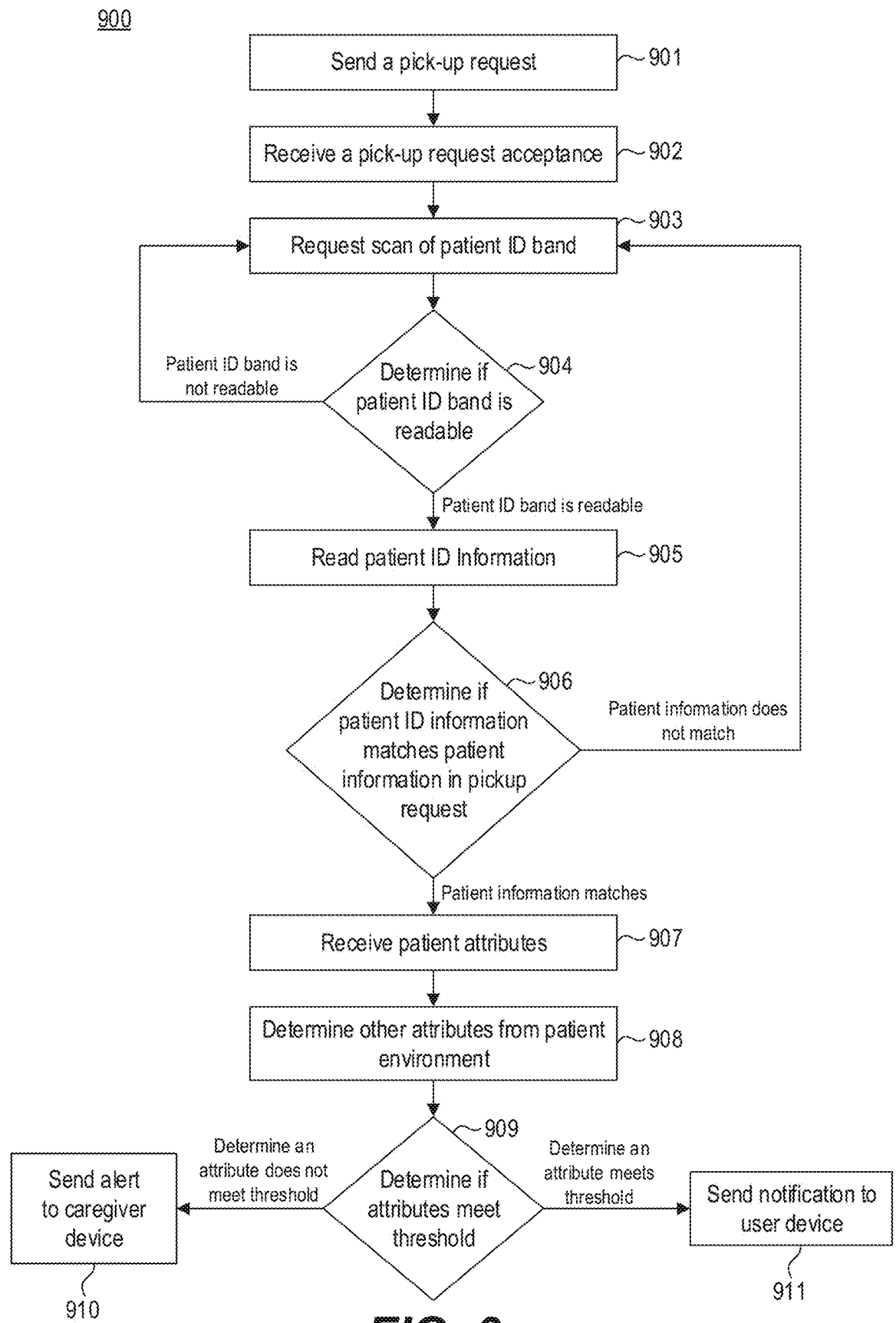
FIG. 9 is a flowchart of an example of steps of the exemplary caregiver transport tracking process of FIGS. 3-8, consistent with embodiments of the present disclosure.

FIG. 9 shows a flowchart of an example of the exemplary caregiver transport tracking process associated with the graphical user interfaces of FIGS. 3-8. Process 900 may be carried out by a number of devices, such as second user device 122 or other devices shown in FIG. 1, that are associated with a caregiver who initiates a new transport request. Thus, the user device and associated caregiver may be located at the location where the patient is to be picked up for transport.

Process 900 may begin in step 901 when a device, such as a second user device 122, generates and sends a pick-up request for a new transport task. In some embodiments, the pick-up request may contain information associated with a patient in need of transportation to a receiving unit within a hospital. This information may include the patient's condition, a patient identifier, the destination of the patient, or the reason for the patient's transport. In some embodiments, the pick-up request may be sent to first user device 120 associated with the transporter, or another device in system 100 such as facility server 130. Following receipt of the pick-up request, a processor of first user device 120 or facility server 130 may analyze the received request and select a handoff protocol for the particular transport request. In some embodiments, the handoff protocol may be automatically selected by applying one or more rule sets or lookup tables to identify handoff steps and information checklists associated with the patient's condition, origin and destination locations, equipment to be transported with the patient, and other predetermined considerations associated with the caregiver, facility characteristics, and patient attributes.

In step 902, a second user device 122 may receive a pick-up request acceptance indication, which may include patient information contained in the original request. In some embodiments, the pick-up request acceptance may contain additional information associated with a patient in need of transportation to a receiving unit within a hospital, such as the amount of oxygen in the patient's oxygen tank, or whether the patient's sensor cables, lines, drains, and tubes are secure. In some embodiments, the pick-up request acceptance may be received from first user device 120, which may be associated with a user 125 such as the transporter, or another device in system 100 such as from facility server 130.

In step 903, second user device 122 may request a scan of a patient ID band as part of a process to confirm that the correct patient is with a user 127, who may be a nurse associated with second user device 122. As discussed above, disclosed embodiments may require both the transporter's user device (120) and the caregiver's device (122) to collect patient identification information, for a multi-faceted verification that the correct patient will be transported. By requiring both devices to collect patient identification information followed by verification by a processor such as facility server 130, the disclosed embodiments may provide for greatly increased accuracy and efficiency in the patient handoff process, as well as an enhanced experience for the transporter, caregiver, and the patient. A patient ID band may be a wristband tied around a patient's wrist, or other scannable identifier that is unique to the patient. In some embodiments, collected patient information may include information obtained using a sensor device such as biometric information including fingerprints, retinal scans, voice waveforms, or faceprints such as those used by Apple Face ID and other known facial recognition techniques. In some embodiments, second user device 122 may request a second form of patient-identifying information for two-step verification of the patient, such as data related to a patient's age, appearance, gender, and any other identifying information particular to the patient.

In step 904, second user device 122 may receive image data, and analyze the image data to detect a computer-readable patient ID band. If second user device 122 determines that there is no computer-readable patient ID band contained in the image data, it may revert to step 903 and request another scan attempt of a patient ID band. In some embodiments, second user device 122 may permit entry of other patient-identifying information regardless of the number of unsuccessful scan attempts. In other embodiments, second user device 122 may only permit entry of this information rather than a scan only if a certain number of scans have been attempted.

In step 905, second user device 122 may read the information contained in a patient ID band and may store it as data within data 246. This information may include a patient's name, date of birth, age, Social Security number, or medical identification number.

In step 906, second user device 122 may compare the information received as a result of the scan of a patient ID band with other already-stored patient data. This already-stored data may be contained in data 242 of a first user device 120 or second user device 122, or it may also be contained within another device in system 100, such as facility server 130 or database 180. In some embodiments, already-stored patient data may not be found in its expected place within system 100, and second user device 122 may perform a search to find patient data to which it can compare the patient information it received as a result of the scan of the patient ID band. Other devices, such as facility server 130, may also perform a search to find patient data, and may send that data to second user device 122. If second user device 122 determines that the patient-identifying data it received in step 902 matches the data received in step 905, it may proceed to step 907. If second user device 122 determines that the patient-identifying data it received in step 902 and the data it received in step 905 do not match, it may return to step 903 and request a scan of a patient ID band.

In step 907, second user device 122 may receive patient attributes from a user 127, such as a nurse. This patient attributes might include information about a patient's medication information, an indication of destination verification, or an indication of medical record verification. Second user device 122 may receive these attributes as a result of a user 127 interacting with a GUI such as the one described with respect to FIG. 6.

In step 908, second user device 122 may receive attributes related to a patient's environment, such as from sensors related to monitoring the patient. These sensors may monitor patient conditions such as heartbeat, blood oxygen saturation level, or temperature. In some embodiments, these attributes may indicate current information related to a patient. In other embodiments, these attributes may have been previously recorded and stored on a device such as facility server 130 or network server 160.

In step 909, second user device 122 may determine whether these attributes meet a pre-determined threshold. For example, in some embodiments second user device 122 may determine that, a patient's current heartbeat falls above a safe threshold, and the patient should not be transported. Second user device 122 may examine patient attributes and attributes from the patient's environment collectively. For example, second user device 122 may determine that a patient has recently taken a medication to reduce the patient's temperature, but that recent recorded attributes indicate that the patient's temperature has not decreased as quickly as expected. In this circumstance, second user device 122 may determine that the patient's rate of recovery has not progressed quickly enough to meet a desired threshold prior to transportation. If second user device 122 determines that an attribute or combination of attributes do not meet pre-determined thresholds, it may proceed to step 910. If second user device 122 determines that all necessary attributes meet pre-determined thresholds, it may proceed to step 911.

In step 910, second user device 122 sends an alert to a caregiver device. This alert may contain information relating to the attributes that did not meet a pre-determined threshold, so that a caregiver or other individual may take appropriate action to care for the patient. In some embodiments, second user device 122 may also send this alert to other devices in system 100, such as computer terminal 140. This alert may prevent second user device 122 from returning to another step in process 900 until the identified attribute or attributes meet a pre-determined threshold.

In step 911, second user device 122 may send a notification to a user device such as first user device 120, which may be associated with a user 125, who may be a transporter in a hospital. The notification may indicate to user 125 that second user device 122 has successfully completed process 900. This notification may be sent with a release command to a device such as first user device 120, such that a halt command on that device is released, and first user device 120 may proceed to new step in a process it is running. In this way, process 900 ensures that all required data input and verifications are completed before advancing the handoff protocol, such as by pausing the protocol until second user device 122 or facility server 130 indicates successful confirmation of patient information, which may be related to the patient's identity, health, and safety.

Figure 10:
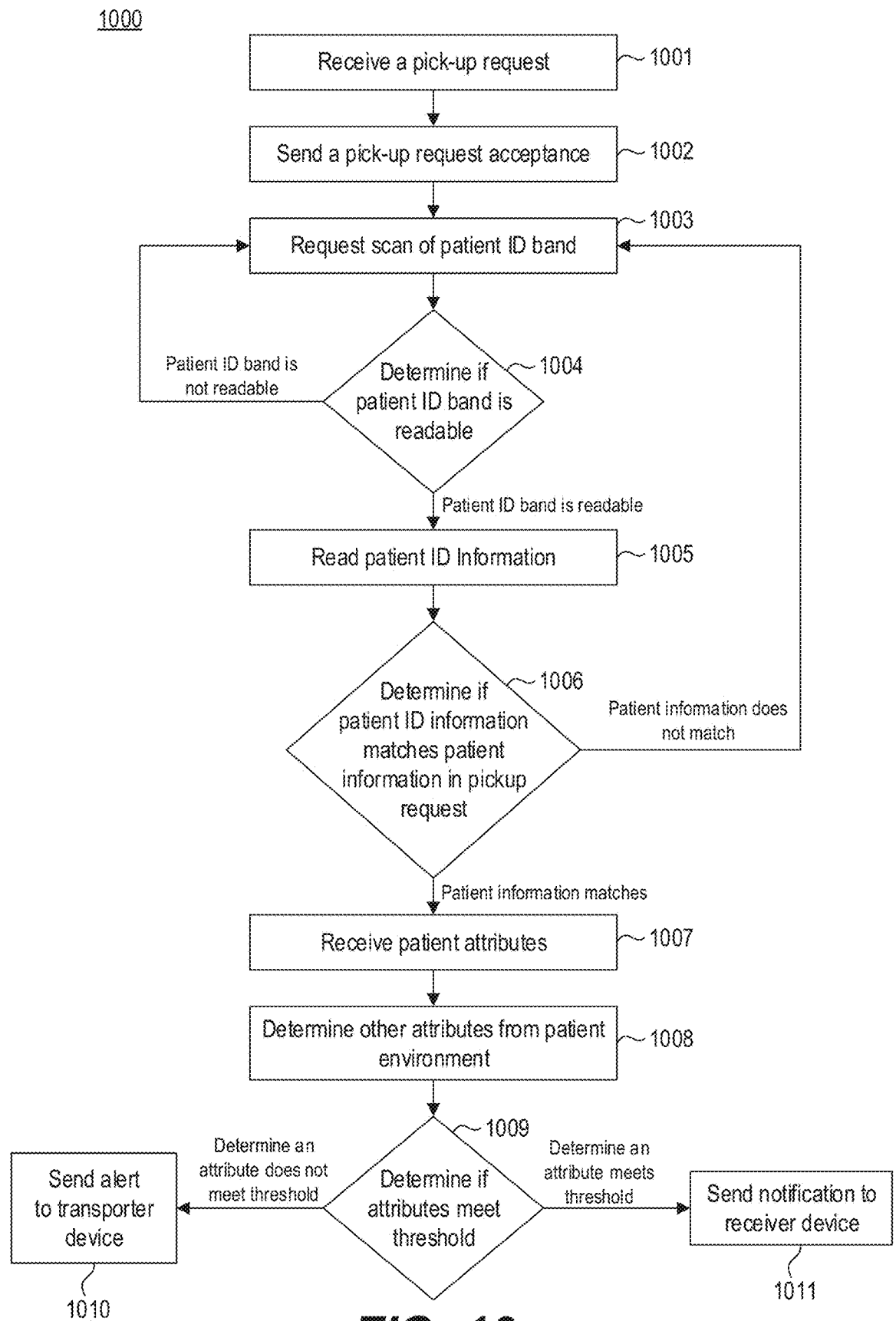
FIG. 10 is a flowchart of an example of steps of the exemplary transporter tracking process of FIGS. 3-8, consistent with embodiments of the present disclosure.

FIG. 10 shows a flowchart of an example of the exemplary transporter tracking process associated with the GUIs shown in FIGS. 3-8. This process may be carried out by a user device associated with a transporter such as first user device 120 or another device shown in FIG. 1.

Process 1000 may begin in step 1001 when a device, such as a first user device 120, receives a pick-up request for a new transport task. Prior to receiving the pick-up request, a processor such as facility server 130 or a processor of second user device 122 (associated with a requesting caregiver) may select a handoff protocol based on attributes of the patient, the facility, and the patient condition. In some embodiments, the pick-up request may contain information associated with a patient in need of transportation to a receiving unit within a hospital, such as the patient's condition, a patient identifier, the destination of the patient, or the reason for the patient's destination. In some embodiments, the pick-up request may be sent from second user device 122 associated with a sending/requesting caregiver w such as a nurse, or from another requesting device in system 100. In some embodiments, the request, which may be a HL7 message used for transferring electronic data between different healthcare computer systems, may be generated automatically by facility server 130, or by another device in system 100, based on a predetermined itinerary or treatment schedule for the patient, indicating that the patient should be moved between locations in the hospital to advance through predetermined treatment itinerary.

In step 1002, a first user device 120 may send a pick-up request acceptance along with patient information related to the pick-up. In some embodiments, the pick-up request acceptance may contain additional information associated with a patient in need of transportation to a receiving unit within a hospital, such as the amount of oxygen in the patient's oxygen tank, or whether the patient's lines, drains, and tubes are secure. In some embodiments, the pick-up request acceptance may have been sent to a second user device 122, which may be associated with a user 127, who may be a nurse, or another device in system 100.

In step 1003, first user device 120 may request a scan of a patient ID band as part of a process to confirm that the correct patient is with a user 125, who may be a transporter associated with first user device 120. A patient ID band may be a wristband tied around a patient's wrist, or other scannable identifier that is unique to the patient. In some embodiments, first user device 120 may request another form of patient-identifying information, such as data related to a patient's age or appearance.

In step 1004, first user device 120 may receive image data, which it examines to determine if it contains a computer-readable patient ID band. If first user device 120 determines that there is no computer-readable patient ID band contained in the image data, it may revert to step 1003 and request another scan attempt of a patient ID band. In some embodiments, first user device 120 may permit entry of other patient-identifying information regardless of the number of unsuccessful scan attempts. In other embodiments, first user device 120 may only permit entry of this information rather than a scan only if a certain number of scans have been attempted.

In step 1005, first user device 120 may read the information contained in a patient ID band and may store it as data within data 246. This information may include a patient's name, date of birth, age, Social Security number, or medical identification number.

In step 1006, first user device 120 may compare the information received as a result of the scan of a patient ID band with other already-stored patient data. This already-stored data may be contained in data 242 of a first user device 120 or second user device 122, or it may also be contained within another device in system 100, such as facility server 130 or database 180. In some embodiments, already-stored patient data may not be found in its expected place within system 100, and first user device 120 may perform a search to find patient data to which it can compare the patient information it received as a result of the scan of the patient ID band. Other devices, such as facility server 130, may also perform a search to find patient data, and may send that data to first user device 120. If first user device 120 determines that the patient-identifying data it received in step 1002 matches the data received in step 1005, it may proceed to step 1007. If first user device 120 determines that the patient-identifying data it received in step 1002 and the data it received in step 1005 do not match, it may return to step 1003 and request a scan of a patient ID band.

In step 1007, first user device 120 may receive patient attributes from a user 125, such as a transporter. This patient attributes might include information about the pressure or flow rate of oxygen in the patient's oxygen tank, or whether the patient's lines, drains, and tubes are secure. First user device 120 may receive these attributes as a result of a user 125 interacting with a GUI such as the one described with respect to FIG. 6.

In step 1008, first user device 120 may receive attributes related to a patient's environment, such as from sensors related to monitoring the patient. These sensors may monitor patient conditions such as heartbeat, blood oxygen saturation level, or temperature. In some embodiments, these attributes may indicate current information related to a patient. In other embodiments, these attributes may have been previously recorded and stored on a device such as facility server 130 or network server 160.

In step 1009, first user device 120 may determine whether these attributes meet a pre-determined threshold. For example, in some embodiments first user device 120 may determine that, a patient's current heartbeat falls above a safe threshold, and the patient should not be transported. First user device 120 may examine patient attributes and attributes from the patient's environment collectively. For example, first user device 120 may determine that a patient was recently connected to received important fluids intravenously, and that the patient's tubes are not secure, and therefore those attributes fail to meet a safe threshold prior to transportation. If first user device 120 determines that an attribute or combination of attributes do not meet pre-determined thresholds, it may proceed to step 1010. If first user device 120 determines that all necessary attributes meet pre-determined thresholds, it may proceed to step 1011.

In step 1010, first user device 120 may send an alert notification to a caregiver device. This alert may contain information relating to the attributes that did not meet a pre-determined threshold, so that a transporter or other individual may take appropriate action to care for the patient. In some embodiments, first user device 120 may also send this alert to other devices in system 100, such as computer terminal 140. This alert may prevent first user device 120 from returning to another step in process 1000 until the identified attribute or attributes meet a pre-determined threshold.

In step 1011, first user device 120 sends a notification to a user device. This notification may be sent to a second user device 122, which may be associated with a user 127, who may be a nurse in a hospital. The notification may indicate to user 127 that first user device 120 has successfully completed process 1000. This notification may be sent with a release command to a device such as second user device 122, such that a halt command on that device is released, and second user device 122 may proceed to new step in a process it is running. In this way, process 1000 ensures that the handoff protocol does not progress until first user device 120 indicates successful confirmation of patient information, which may be related to the patient's identity, health, and safety.

Figure 11:
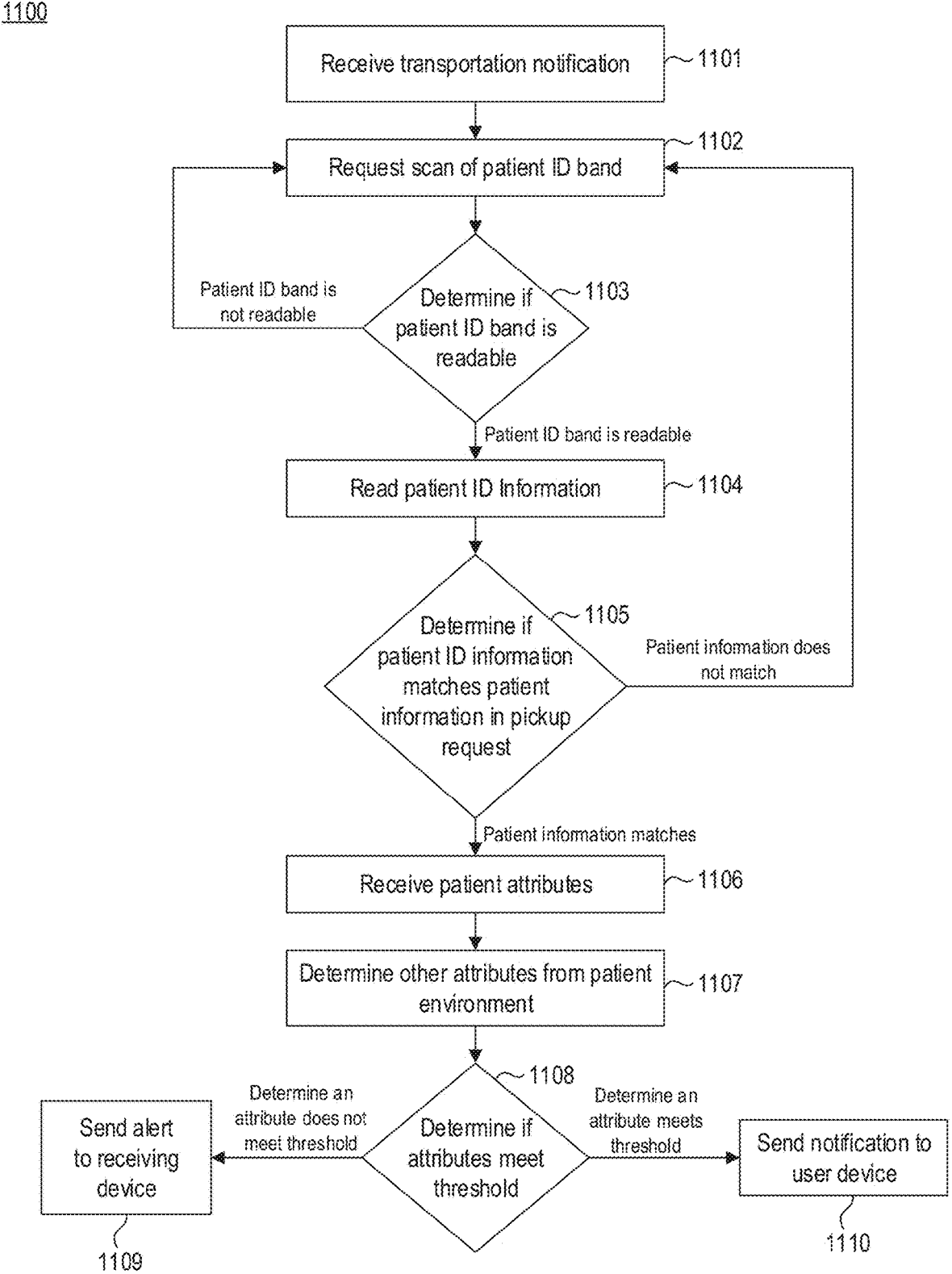
FIG. 11 is a flowchart of an example of steps of the exemplary transport arrival tracking process of FIGS. 3-8, consistent with embodiments of the present disclosure

FIG. 11 shows a flowchart of an exemplary transport arrival tracking process of FIGS. 3-8, consistent with embodiments of the present disclosure. The transport arrival tracking process may be carried out by a number of devices, such as first user device 120 associated with a transporter user, and another user device associated with a receiving caregiver such as devices shown in FIG. 1. In the example discussed below, the receiving caregiver's device is identified as second user device 122, but it is to be understood that the receiving caregiver and associated user device may be different from the sending/requesting caregiver and associated device. It is also to be understood that while process 1100 is described in connection with second user device 122, first user device 120 may also perform steps of process 1100 other than step 1101. By performing process 1100 simultaneously or nearly simultaneously on both electronic user devices, the disclosed systems may provide for enhanced accuracy and efficiency by ensuring consistency between received and sensed data, thereby also enhancing the experience of the transporter, caregiver(s), and the patient.

Process 1100 may begin in step 1101, when a second user device 122 may receive a transportation arrival notification, which may be sent from first user device 120 associated with the transporter or from facility server 130. In some embodiments, the transportation arrival notification may indicate that the transported patient has arrived at the destination, or is expected to arrive at the destination within a predetermined amount of time. The transportation arrival notification may also provide information associated with a patient in need of transportation to a receiving unit within a hospital, such as the patient's destination or a critical status. In some embodiments, the transportation arrival notification may be generated and transmitted by first user device 120, or another device in system 100 such as facility server 130 or computer terminal 140.

In step 1102, second user device 122 may request a scan of a patient ID band as part of a process to confirm that the patient identified in the handoff protocol is in fact the same patient that just arrived at the destination with the transporter. A patient ID band may be a wristband tied around a patient's wrist, or other scannable identifier that is unique to the patient. In some embodiments, second user device 122 may request another form of patient-identifying information, such as data related to a patient's age or appearance.

In step 1103, second user device 122 may receive image data, which it examines to determine if it contains a computer-readable patient ID band. If second user device 122 determines that there is no computer-readable patient ID band contained in the image data, it may revert to step 1102 and request another scan attempt of a patient ID band. In some embodiments, second user device 122 may permit entry of other patient-identifying information regardless of the number of unsuccessful scan attempts. In other embodiments, second user device 122 may only permit entry of this information rather than a scan only if a certain number of scans have been attempted.

In step 1104, second user device 122 may read the information contained in a patient ID band and may store it as data within data 246. This information may include a patient's name, date of birth, age, Social Security number, or medical identification number.

In step 1105, second user device 122 may compare the information received as a result of the scan of a patient ID band with other already-stored patient data. This already-stored data may be contained in data 242 of a first user device 120 or second user device 122, or it may also be contained within another device in system 100, such as facility server 130 or database 180. In some embodiments, already-stored patient data may not be found in its expected place within system 100, and second user device 122 may perform a search to find patient data to which it can compare the patient information it received as a result of the scan of the patient ID band. Other devices, such as facility server 130, may also perform a search to find patient data, and may send that data to second user device 122. If second user device 122 determines that the patient-identifying data it received in step 1102 matches the data received in step 1105, it may proceed to step 1106. If second user device 122 determines that the patient-identifying data it received in step 1101 and the data it received in step 1105 do not match, it may return to step 1102 and request a scan of a patient ID band.

In step 1106, second user device 122 may receive patient attributes from a user 127, such as a receiver. This patient attributes might include information concerning the pressure or flow rate of oxygen in the patient's oxygen tank, or an indication of whether a patient's needs are met for testing. Second user device 122 may receive these attributes as a result of a user 127 interacting with a GUI such as the one described with respect to FIG. 6.

In step 1107, second user device 122 or facility server 130 may receive attributes related to a patient's environment, such as from sensors related to monitoring the patient. These sensors may monitor patient conditions such as heartbeat, blood oxygen saturation level, or temperature. In some embodiments, these attributes may indicate current information related to a patient. In other embodiments, these attributes may have been previously recorded and stored on a device such as facility server 130 or network server 160.

In step 1108, second user device 122 may determine whether these attributes meet a pre-determined threshold. For example, in some embodiments second user device 122 may determine that, a patient's oxygen tank does not have sufficient oxygen based on the length of the patient's planned visit at a receiving unit. Second user device 122 may examine patient attributes and attributes from the patient's environment collectively. For example, second user device 122 may determine that a patient has recently taken a medication to reduce the patient's temperature, but that recent recorded attributes indicate that the patient's temperature has not decreased as quickly as expected. In this circumstance, second user device 122 may determine that the patient's rate of recovery has not progressed quickly enough to meet a desired threshold prior to transportation. If second user device 122 determines that an attribute or combination of attributes do not meet pre-determined thresholds, it may proceed to step 1109. If second user device 122 determines that all necessary attributes meet pre-determined thresholds, it may proceed to step 1110.

In step 1109, second user device 122 sends an alert to a receiving device. This alert may contain information relating to the attributes that did not meet a pre-determined threshold, so that a receiver or other individual may take appropriate action to care for the patient. In some embodiments, second user device 122 may also send this alert to other devices in system 100, such as computer terminal 140. This alert may prevent second user device 122 from returning to another step in process 1100 until the identified attribute or attributes meet a pre-determined threshold.

In step 1110, second user device 122 sends a notification to a user device. This notification may be sent to a first user device 120, which may be associated with a user 125, who may be a transporter in a hospital. The notification may indicate to user 125 that second user device 122 has successfully completed process 1100. This notification may be sent with a release command to a device such as first user device 120, such that a halt command on that device is released, and first user device 120 may proceed to new step in a process it is running. In this way, process 1100 ensures that another user may not progress in a patient transport process until second user device 122 indicates successful confirmation of patient information, which may be related to the patient's identity, health, and safety.

What is claimed is:

1. A computerized system, comprising:
  a memory storing instructions; and
  a processor of a first electronic device in communication with a network, the processor configured to execute the stored instructions to:
    receive, from a second electronic device via the network, a pick-up request, wherein the pick-up request comprises a request to transport a patient within a healthcare facility, wherein the patient has a corresponding handoff protocol for the transportation;
    receive, via an input device in communication with the processor, an acceptance indication for the pick-up request;

provide a graphical user interface prompting a user to scan an identification tag on an individual, the graphical user interface including at least one button that is in a non-selectable state;

capture, using the first electronic device, an image of the identification tag;

determine, based on the captured identification tag image, an identity of the individual;

verify the identity of the individual by comparing the determined identity to an identity in the received pick-up request;

modify the graphical user interface to change the at least one button to a selectable state, wherein selection of the at least one button advances the first electronic device to a first next step in a handoff protocol for the individual; and determine at least one environment attribute from an environment of the patient and determine whether the at least one environment attribute meets a predefined threshold;

advance, based on a determination that the at least one environment attribute meets the predefined threshold, advancing the first electronic device to a second next step in a handoff protocol for the patient, wherein the advancing comprises sending a notification to a third user device.

2. The system of claim 1, wherein advancing the first electronic device to the first next step in the handoff protocol for the individual comprises receiving at least one trait attribute associated with the individual.

3. The system of claim 2, wherein the individual is a patient in a hospital and the at least one trait attribute is a condition of the patient.

4. The system of claim 1, wherein the at least one environment attribute is determined from at least one sensor monitoring the individual.

5. The system of claim 4, wherein the at least one sensor monitors at least one of a heartbeat, blood oxygen saturation level, or temperature of the individual.

6. The system of claim 1, wherein the predefined threshold is based on the at least one trait attribute.

7. The system of claim 1, wherein advancing the first electronic device to the second next step comprises releasing a halt command on a third user device.

8. The system of claim 1, the instructions further comprising, based on a determination that the at least one environment attribute does not meet the predefined threshold, sending an alert to a third user device.

9. The system of claim 1, wherein the determination of the identity of the individual is based on information contained in the captured identification tag image, the information comprising at least one of: the individual's name, date of birth, age, Social Security number, or medical identification number.

10. A method for a handoff protocol, the method comprising:

receiving, at a first electronic device from a second electronic device via a network, a pick-up request, wherein the pick-up request comprises a request to transport a patient within a healthcare facility, wherein the patient has a corresponding handoff protocol for the transportation;

receiving, via an input device, an acceptance indication for the pick-up request;

providing a graphical user interface prompting a user to scan an identification tag on an individual, the graphical user interface including at least one button that is in a non-selectable state;

capturing, using the first electronic device, an image of the identification tag;

determining, based on the captured identification tag image, an identity of the individual;

verifying the identity of the individual by comparing the determined identity to an identity in the received pick-up request;

modifying the graphical user interface to change the at least one button to a selectable state, wherein selection of the at least one button advances the first electronic device to a first next step in a handoff protocol for the individual; and determining at least one environment attribute from an environment of the patient and determine whether the at least one environment attribute meets a predefined threshold;

advancing, based on a determination that the at least one environment attribute meets the predefined threshold, advancing the first electronic device to a second next step in a handoff protocol for the patient, wherein the advancing comprises sending a notification to a third user device.

11. The method of claim 10, wherein advancing the first electronic device to the first next step in the handoff protocol for the individual comprises receiving at least one trait attribute associated with the individual.

12. The method of claim 10, wherein the at least one environment attribute is determined from at least one sensor monitoring the individual.

13. A non-transitory computer-readable medium including instructions that, when executed by a processor, cause the at least one processor to perform operations comprising:

receiving, at a first electronic device from a second electronic device via a network, a pick-up request, wherein the pick-up request comprises a request to transport a patient within a healthcare facility, wherein the patient has a corresponding handoff protocol for the transportation;

receiving, via an input device, an acceptance indication for the pick-up request;

providing a graphical user interface prompting a user to scan an identification tag on an individual, the graphical user interface including at least one button that is in a non-selectable state;

capturing, using the first electronic device, an image of the identification tag;

determining, based on the captured identification tag image, an identity of the individual;

verifying the identity of the individual by comparing the determined identity to an identity in the received pick-up request;

modifying the graphical user interface to change the at least one button to a selectable state, wherein selection of the at least one button advances the first electronic device to a first next step in a handoff protocol for the individual; and determining at least one environment attribute from an environment of the patient and determine whether the at least one environment attribute meets a predefined threshold;

advancing, based on a determination that the at least one environment attribute meets the predefined threshold, advancing the first electronic device to a second next step in a handoff protocol for the patient, wherein the advancing comprises sending a notification to a third user device.

\* \* \* \* \*